United States Patent [19]

Morante

[11] Patent Number: 4,905,713

[45] Date of Patent: Mar. 6, 1990

[54] SHOULDER MOVEMENT RESTRICTION DEVICE

[76] Inventor: Debrah A. Morante, 109 Guyer Ave., Lavallette, N.J. 08735

[21] Appl. No.: 298,966

[22] Filed: Jan. 19, 1989

[51] Int. Cl.⁴ ............................................. A61F 13/00
[52] U.S. Cl. .................................... 128/875; 128/878; 128/77; 128/94
[58] Field of Search ................. 128/77, 874, 875, 876, 128/877, 878

[56] References Cited

U.S. PATENT DOCUMENTS

| | | | |
|---|---|---|---|
| 3,324,851 | 6/1967 | Posner | 128/878 |
| 3,970,316 | 7/1976 | Westmoreland, Jr. | 273/189 R |
| 4,172,453 | 10/1979 | Leckie | 128/878 |
| 4,436,088 | 3/1984 | Finnleston | 128/77 |
| 4,598,703 | 7/1986 | Lindemann | 128/94 |
| 4,610,244 | 9/1986 | Hammond | 128/77 |
| 4,662,366 | 5/1987 | Tari | 128/877 |
| 4,735,198 | 4/1988 | Sawa | 128/878 |
| 4,751,923 | 6/1988 | Marino | 128/94 |

Primary Examiner—Robert A. Hafer
Assistant Examiner—Lynda M. Cofsky
Attorney, Agent, or Firm—Fleit, Jacobson, Cohn, Price, Holman & Stern

[57] ABSTRACT

A shoulder movement restriction device to control the range of motion of the shoulder to prevent excess movement while the wearer is participating in various sports activities including contact sports such as football and other sports in which it is desired to limit the range of motion of the shoulder due to a recent injury or a history of chronic subluxation of the shoulder. The restriction device includes a substantially rigid but yet slightly flexible U-shaped member with a foam plastic liner secured to the U-shaped member to cushion engagement with the arm of the wearer with an adjustable webbing strap encircling the restriction device and securing it in place around the arm of the wearer between the shoulder and elbow with a chest arrangement connected to the device to retain the upper arm against the side of the chest and preventing excessive movement of the arm about the shoulder joint.

8 Claims, 1 Drawing Sheet

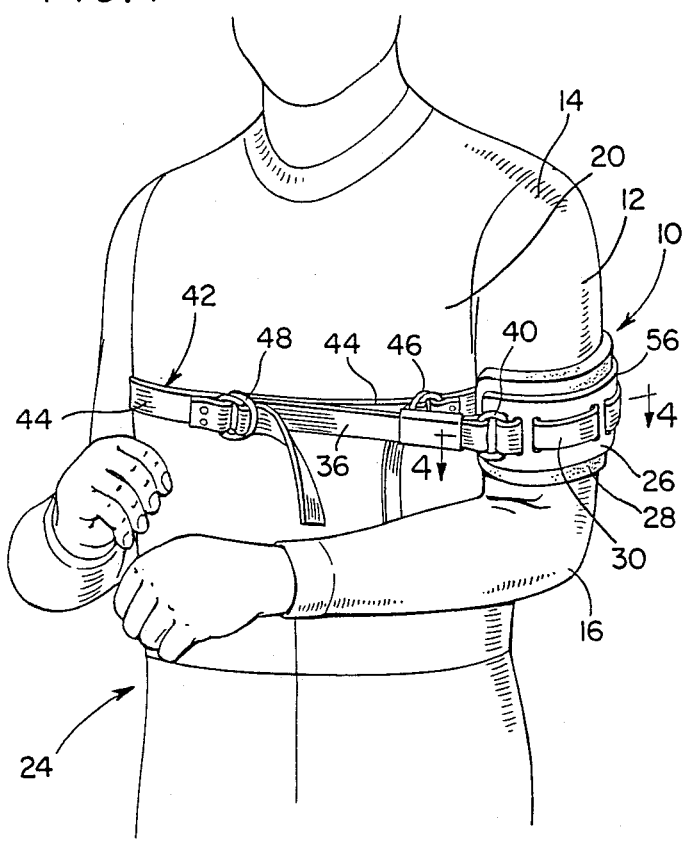

SHOULDER MOVEMENT RESTRICTION DEVICE

BACKGROUND OF THE INVENTION

1. Field of the Invention

The present invention generally relates to a restraining device for supporting and substantially immobilizing an injured limb of a patient and more particularly a shoulder movement restriction device to control the range of motion of the shoulder to prevent excess movement while the wearer is participating in various sports activities including contact sports such as football and other sports in which it is desired to limit the range of motion of the shoulder due to a recent injury or a history of chronic subluxation of the shoulder. The restriction device includes a substantially rigid but yet slightly flexible U-shaped member with a foam plastic liner secured to the U-shaped member to cushion engagement with the arm of the wearer with an adjustable webbing strap encircling the restriction device and securing it in place around the arm of the wearer between the shoulder and elbow with a chest arrangement connected to the device to retain the upper arm against the side of the chest and preventing excessive movement of the arm about the shoulder joint.

2. Information Disclosure Statement

Many patents exist that disclose devices for attachment to the extremities or limbs of a human being to support and/or immobilize the limb. Such devices include various types of casts, splints and slings. However, the prior patents do not disclose a structure especially adapted to restrict movement of the shoulder in situations where the shoulder joint has been dislocated. The following U.S. Pat. Nos. are relevant to the above invention but do not disclose the same or equivalent structure.

3,788,307
4,422,455
4,436,088
4,598,703
4,610,244

SUMMARY OF THE INVENTION

An object of the present invention is to provide a shoulder movement restriction device for controlling excess movement of the shoulder during treatment of shoulder subluxation with the device including an assembly disposed in encircling relation to the upper arm between the shoulder and elbow that is connected to a body or chest harness in a manner to retain the upper arm adjacent the side surface area of the chest cavity and limiting movement of the upper arm about the shoulder joint in all directions of movement capability.

Another object of the invention is to provide a restriction device in accordance with the preceding object in which the assembly which encircles the upper arm includes a heat molded plastic member of generally U-shaped configuration having a heat molded foam plastic cushion secured along the inner surface thereof to engage the upper arm and an adjustable strap to secure the assembly in encircling relation to the upper arm without clamping it tightly against the upper arm which would tend to restrict blood flow.

A further object of the invention is to provide a restriction device in accordance with the preceding objects in which the U-shaped member is substantially rigid but sufficiently flexible to enable it to be placed over the upper arm and the foam plastic liner is interposed between the substantially rigid U-shaped member and the upper arm.

Still another object of the invention is to provide a restriction device in accordance with the preceding objects which can be easily assembled onto the upper arm and connected to various types of chest or body harnesses to restrict movement of the arm about the shoulder joint in an effective manner with the device being easily placed in position and removed.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a front perspective view of the shoulder movement restriction device of the present invention.

FIG. 2 is a rear elevational view thereof.

FIG. 3 is a perspective view of the upper arm encircling device with the closure web strap and chest harness engaging straps attached thereto.

FIG. 4 is a transverse, sectional view, on an enlarged scale, taken substantially upon a plane passing along section line 4—4 on FIG. 1 illustrating the structure of the restriction device and its association with the upper arm and chest cavity.

DESCRIPTION OF THE PREFERRED EMBODIMENT

Referring now specifically to the drawings, the shoulder movement restriction device of the present invention is generally designated by reference numeral 10 and is positioned in encircling relation to a portion of the upper arm 12 between the shoulder 14 and elbow 16 in order to retain the upper arm 12 adjacent the chest 20 with the arm being positioned closely adjacent the side surface of the chest wall 22 as illustrated in FIG. 4. The restriction device 10 is primarily used for controlling and limiting the range of movement of the upper arm 12 about the shoulder joint 14 to prevent an excess in the range of movement of upper arm 12 when the user 24 is engaged in various activities including sports activities such as contact sports including football and the like and various non-contact sports where it is desirable to restrict movement of the upper arm 12 while permitting various activities to be performed with the other arm and hand. The restriction device 10 controls and limits motion of the shoulder 14 after shoulder dislocation or if a user has a history of chronic subluxation of the shoulder. This enables the user to participate in contact sports such as football and the like and also participate in non-contact sports and various other activities that would normally require movement of the forearm, elbow 16, upper arm 12 and movement of the shoulder joint 14.

The restriction device 10 includes a generally U-shaped plastic member 26 which is a heat molded thermoplastic material identified as perforated "Orthoplast" available from Johnson & Johnson, New Brunswick, N.J. A second component of the restriction device 10 is a cushioning member 28 of foam plastic extending interiorly of the substantially rigid U-shaped plastic member 26. The foam plastic cushioning member 28 is also a heat molded material and is identified as "Plastizote" and is available from United Foam Products, Inc. Another component of the restriction device is a cotton webbing strap 30 disposed against the outer surface of plastic member 26 and provided with D-rings 32 at one end thereof. Additional cotton webbing straps 34 and 36 are attached to the cotton webbing strap 30 by the use of D-rings 38 and 40 which are spaced from the ends of strap 30 as illustrated in FIG. 4. The strap 34 extends posteriorly and is attached to buckle 50 so as to control external rotation of the upper arm while strap 36 extends anteriorly and attaches to buckle 48 which stabilizes the upper arm. A harness generally designated by the numeral 42 which includes a chest strap 44 of webbing secured adjustably by buckle 46 and connected to the straps 34 and 36 by a connecting buckle 48 at the front and a connecting buckle 50 at the rear. Various types of criss-cross arrangements of chest harnesses may be utilized to securely anchor the restriction device 10 in place with such devices including harnesses that encircle the chest cavity to retain the attaching straps 34 and 36 in place across the front and rear of the chest 20.

The foam material of cushioning member 28 may be on the order of ½" thick and a piece of foam material 12" long and 6" wide may be cut from a large panel or otherwise supplied and is placed in an oven and softened by a heat level that will soften the foam but not burn the material. While the foam is still in a softened condition, but not sufficiently hot to burn the upper arm, the foam material is applied to the upper arm 12 of the user 24 to obtain an appropriate mold of the foam material to the size and contour of the exterior of the upper arm with the end edges of the foam material being curved at the corners and being spaced from each other along the inner surface of the upper arm 12 as illustrated in FIG. 4 with the ends of the foam plastic being designated by reference numeral 52. Then, the plastic panel 26 which has a width and length less than the cushioning member 28 is placed in hot water at approximately 180 degrees Fahrenheit and softened and then applied around the molded foam cushioning member 28 which had been previously formed so that when the plastic member 26 hardens, it will be substantially U-shaped with the end edges 54 spaced approximately ½" from the end edges 52 and the top and bottom edges 56 of the plastic member being spaced from the top and bottom edges of the foam material by approximately ½". The foam material is trimmed to fit the desired size as may be necessary and to provide rounded corners at the juncture between the end edges and top and bottom edges.

A strap of cotton webbing 30 having a width of 1" and a 12" length is provided and extends through pairs of slits 58 in the plastic member 26 and corresponding slits 60 in the foam material with the webbing 30 being disposed exteriorly of the plastic member 26. As illustrated in FIG. 4, four pairs of slits 58 and 60 are provided in the plastic member 26 and the cushioning member 28 with two of the pairs of slits being closely associated with each other adjacent one end edge 52 of the member 28 to form a loop 62 externally of the plastic member 26 as illustrated in FIG. 4 to secure D-ring 40 to the plastic member 26. One end of the webbing strap 30 terminates in an extended free end portion 64. The other end of the webbing strap 30 is reversely stitched as at 66 to form an end loop 68 to mount the two D-rings 32 to the end of the strap 30 and an intermediate loop 70 to mount the D-ring .38 to the webbing strap 30. The free end 64 of the webbing strap 30 is threaded through the two D-rings 32 to adjustably connect the ends of the webbing strap 30 with this connection being made between the end edges 52 of the member 28 as illustrated in FIG. 4 with this connection being disposed between the inner surface of the upper arm 12 and the chest wall 22. The two cotton webbing straps 34 and 36 are connected respectively to the D-rings 38 and 40 by providing a reversely stitched end portion 72 to form a loop 74 to receive the D-ring 38 and a reversely stitched portion 76 on the strap 36 to form a loop 78 to receive the D-ring 40. The two cotton webbing straps 34 and 36 may be approximately 15" in length and the free ends thereof are connected to the harness 42 through suitable connecting buckles 48 and 50 or by other appropriate connecting means with it being pointed out that the harness 42 may be a chest encircling strap to which the cotton webbing straps 34 and 36 can be adjustably connected thereby limiting and controlling the movement of the upper arm 12 both outwardly, forwardly, rearwardly and rotationally thereby controlling motion or movement in the shoulder joint 14 to maintain the proper relation of the components of the shoulder joint in the event of subluxation of the shoulder joint. This enables the user 24 to participate in various activities where movement of the arm would be involved and even enable the user to participate in various sports activities including non-contact sports and contact sports while reducing the potential for further injury to the shoulder joint.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A shoulder movement restriction device comprising a generally U-shaped, substantially rigid member, a correspondingly shaped cushion along the inner surface of said U-shaped member, a flexible strap positioned along the outer surface of the U-shaped member and provided with ends which bridge the space between the ends of the U-shaped member and cushion for securing the U-shaped member and cushion to the upper arm between the shoulder and elbow of a user and circumferentially spaced slit means in the U-shaped member receiving the strap therethrough for interconnecting the strap, U-shaped member and cushion at circumferentially spaced points to retain them in assembled relation, and means connecting the restriction device to a body harness to restrict movement of the upper arm about the shoulder joint when the shoulder joint has been subjected to subluxation.

2. The structure as defined in claim 1 wherein said means connecting the restriction device to a body harness includes a pair of straps connected to the flexible strap at longitudinally spaced points and extending to and connected with a body harness encircling the chest cavity of the user at points generally oriented at the front center and rear center of the chest cavity.

3. The structure as defined in claim 2 wherein said means connecting the ends of the flexible strap is positioned in the space between the ends of the U-shaped member and cushion with the means connecting the U-shaped member to the cushion including the flexible strap being threaded through spaced slits in the U-shaped member and cushion.

4. The structure as defined in claim 3 wherein said cushion includes a peripheral edge that extends beyond the periphery of the U-shaped member thereby protecting the upper arm from contact with the peripheral edge of the U-shaped rigid member.

5. A shoulder movement restriction device comprising a generally U-shaped, substantially rigid member, a correspondingly shaped cushion along the inner surface of said U-shaped member, a flexible strap positioned along the outer surface of the U-shaped member and provided with ends which bridge the space between the ends of the U-shaped member and cushion for securing the U-shaped member and cushion to the upper arm between the shoulder and elbow of a user and means interconnecting the strap, U-shaped member and cushion to retain them in assembled relation, and means connecting the restriction device to a body harness to restrict movement of the upper arm about the shoulder joint when the shoulder joint has been subjected to subluxation, said rigid member being constructed of heat molded plastic material, said cushion being constructed of heat molded foam plastic material, said means interconnecting the flexible strap, U-shaped member and cushion including a plurality of circumferentially spaced pairs of slits extending through the U-shaped member and cushion, said strap being threaded through the pairs of slits to connect the U-shaped member and cushion with the ends of the strap being free and means adjustably connection the free ends of the strap to secure the U-shaped member and cushion on the upper arm with the spaced ends of the cushion and the means connecting the free ends of the strap being disposed between the inner surface of the upper arm and the chest cavity wall.

6. The structure as defined in claim 5 wherein said foam plastic material forming the cushion has a peripheral edge spaced outwardly from the peripheral edge of the U-shaped member.

7. The structure as defined in claim 6 wherein said means connecting the restriction device to a body harness includes flexible straps connected to the U-shaped member and cushion.

8. The structure as defined in claim 7 wherein said means connecting the free ends of the strap extending around the periphery of the U-shaped member includes a pair of D-rings on one end of the strap and the other end of the strap being threaded through the D-rings and adjustably connected thereto, said straps connected to the body harness being connected to the flexible strap extending around the periphery of the U-shaped member by D-rings.

* * * * *